United States Patent
Adams et al.

(10) Patent No.: US 6,192,104 B1
(45) Date of Patent: Feb. 20, 2001

(54) FAN AND PENCIL BEAMS FROM A COMMON SOURCE FOR X-RAY INSPECTION

(75) Inventors: William Adams, Powell, OH (US); Lee Grodzins, Lexington, MA (US)

(73) Assignee: American Science and Engineering, Inc., Billerica, MA (US)

(*) Notice: Under 35 U.S.C. 154(b), the term of this patent shall be extended for 0 days.

(21) Appl. No.: 09/448,717

(22) Filed: Nov. 24, 1999

Related U.S. Application Data

(60) Provisional application No. 60/110,223, filed on Nov. 30, 1998, and provisional application No. 60/134,413, filed on May 17, 1999.

(51) Int. Cl.[7] .................................................. G01N 23/203
(52) U.S. Cl. ............................ 378/90; 378/57; 378/86; 378/88; 378/149; 378/160
(58) Field of Search .................... 378/51, 53, 54, 378/55, 57, 86, 88, 89, 90, 145, 146, 147, 149, 150, 160

(56) References Cited

U.S. PATENT DOCUMENTS

| | | | |
|---|---|---|---|
| 4,745,631 | 5/1988 | Polini | 378/146 |
| 4,839,913 | * 6/1989 | Annis et al. | 378/44 |
| 4,953,192 | 8/1990 | Plewes | 378/146 |
| 4,995,066 | 2/1991 | Harding et al. | 378/146 |
| 5,038,370 | 8/1991 | Harding et al. | 378/146 |
| 5,260,981 | 11/1993 | Uyama | 378/57 |
| 5,260,982 | 11/1993 | Fujii et al. | 378/87 |
| 5,313,511 | * 5/1994 | Annis et al. | 378/87 |
| 5,493,596 | 2/1996 | Annis | 378/57 |
| 5,600,700 | * 2/1997 | Krug et al. | 378/57 |
| 5,666,393 | * 9/1997 | Annis | 378/57 |
| 5,870,670 | * 9/1989 | Geus | 378/87 |

FOREIGN PATENT DOCUMENTS

WO 99-39189   8/1999   (WO).

OTHER PUBLICATIONS

Patent Abstracts of Japan—JP 05 323039 A (Toshiba Corp.), Dec. 7, 1993.

* cited by examiner

Primary Examiner—David V. Bruce
Assistant Examiner—Allen C Ho
(74) Attorney, Agent, or Firm—Brombert & Sunstein LLP

(57) ABSTRACT

A system and method for inspecting an object, where both a fan beam and a pencil beam of penetrating radiation are used to illuminating the object concurrently. Both beams may be derived from a single source of penetrating radiation. The pencil beam is noncoplanar with the fan beam and may be scanned with respect to the object. Radiation scattered from the pencil beam within the object is detected, and the scatter signal thus generated is used in conjunction with a transmission signal which characterizes attenuation of the fan beam by the object.

10 Claims, 3 Drawing Sheets

PLAN VIEW

PLAN VIEW

TOP VIEW

SIDE VIEW

FAN AND PENCIL BEAMS FROM A COMMON SOURCE FOR X-RAY INSPECTION

This application claims priority from U.S. provisional applications Nos. 60/110,223, filed Nov. 30, 1998, and 60/134,413, filed May 17, 1999, both of which applications are herein incorporated by reference.

TECHNICAL FIELD

The present invention relates to a system and method for inspecting an object with penetrating radiation wherein a source of such radiation provides both a fan beam and a pencil beam that may be scanned across the inspected object.

BACKGROUND OF THE INVENTION

X-ray systems are commonly employed for such applications as the inspection of materials or containers by illuminating the material or container from the outside by means of fan beams. A fan beam refers to a beam having an opening angle in one dimension substantially larger than the width of the beam in a dimension orthogonal to the first. Additionally, the use of a pencil beam, scanned across the object under inspection is also known and used in the art.

The concurrent or alternating application of one or more fan beams and one or more pencil beams is the subject, for example, of copending provisional application No. 60/072,890, filed Jan. 28, 1998, which is herein incorporated by reference.

The methods known in the art for concurrently applying multiple beams require multiple sources penetrating radiation.

SUMMARY OF THE INVENTION

In accordance with one aspect of the invention, in one of its embodiments, there is provided an inspection system for inspecting an object such as a cargo enclosure. The system has a source of penetrating radiation for providing a pencil beam and a fan beam, the pencil beam being noncoplanar with the fan beam. Additionally, the system has a first detector arrangement for detecting penetrating radiation from the fan beam transmitted through the object and generating a transmitted radiation signal. Similarly, the system has a second detector arrangement for detecting penetrating radiation from the pencil beam scattered by the object and generating a scattered radiation signal. Finally, the system has a controller for determining at least one characteristic of the object based at least on the transmitted and scattered radiation signals.

In accordance with alternate embodiments of the invention, the source of penetrating radiation may be an x-ray source, including an x-ray tube or a linear accelerator (LINAC), and may be pulsed or continuous. The system may have a collimator for shaping the fan beam and a scanner arrangement for varying the orientation of the pencil beam with respect to the object. Additionally, the object may be in motion with respect to at least one of the pencil and fan beams.

BRIEF DESCRIPTION OF THE DRAWINGS

The foregoing features of the invention will be more readily understood by reference to the following detailed description taken with the accompanying drawings in which.

DETAILED DESCRIPTION OF PREFERRED EMBODIMENTS

Figure 1:
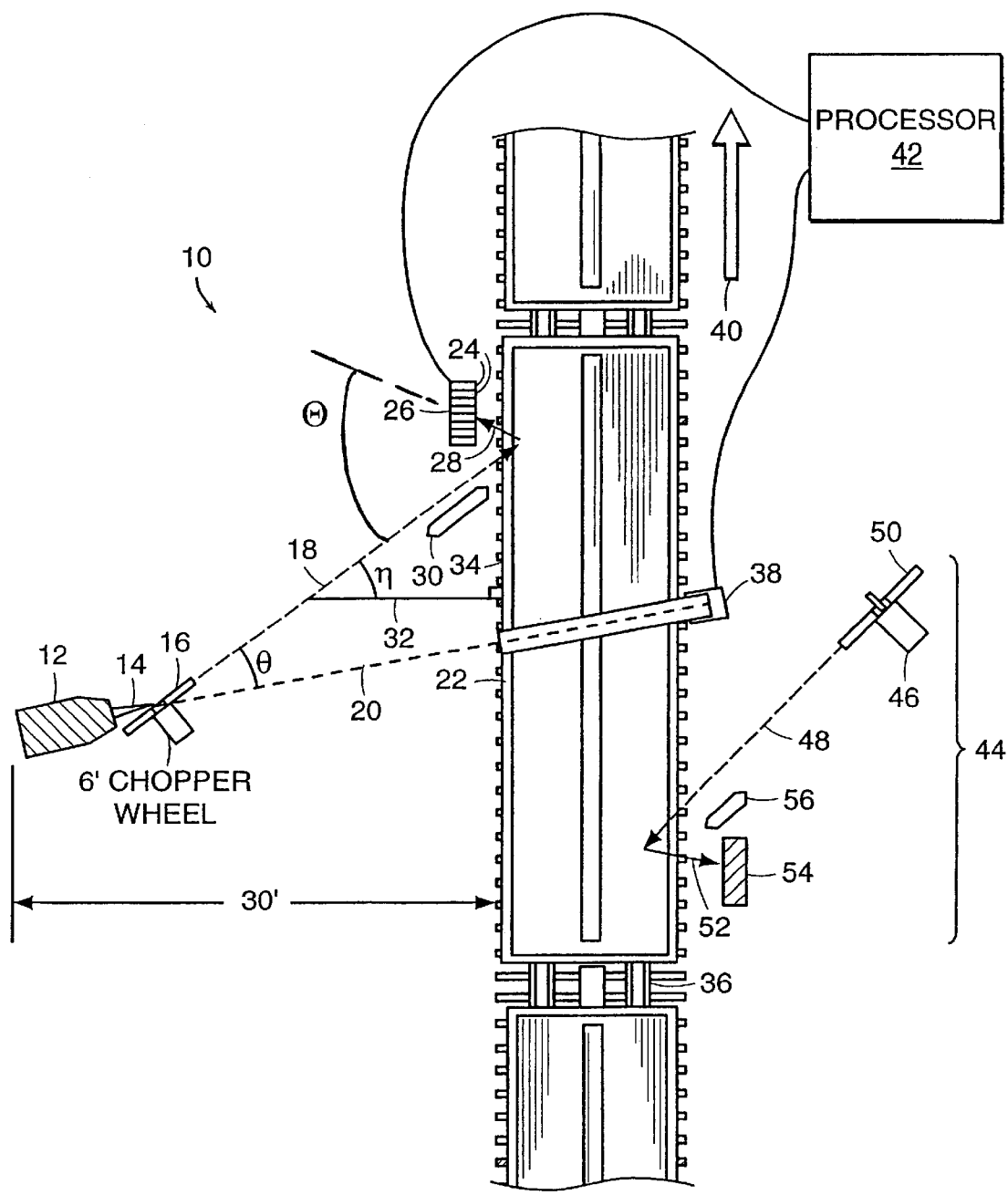
FIG. 1 provides a top view of an inspection system employing two sources of radiation, one of which provides both a fan beam and a pencil beam in accordance with a preferred embodiment of the present invention.

FIG. 1 shows a plan view of the elements of a rapid x-ray inspection system, designated generally by numeral 10. A source 12 emits penetrating radiation in a cone-shaped beam 14. Beam 14 of penetrating radiation, may be, for example, a beam of x-rays such as a polychromatic x-ray beam. Source 12 of penetrating radiation may be a LINAC, for example, or an x-ray tube, for another example. It is preferred that source 12 be a continuous source of penetrating radiation, such as a CW LINAC, for example. For some applications, a pulsed x-ray generator with an appropriate repetition rate may be used. Beam 14 will be referred to in the present description, without limitation, as an x-ray beam. In accordance with a preferred embodiment of the invention, rotating chopper wheel 16 (as described, for example, in copending application U.S. Ser. No. 09/238,686) is used to develop a pencil beam 18 which may be swept in a plane substantially perpendicular to that of the page. The cross section of pencil beam 18 is of comparable extent in each dimension and is typically substantially rectangular. The dimensions of pencil beam 18 typically define the scatter image resolution which may be obtained with the system. A fan beam 20 is also formed from the output of source 12. Fan beam 20 has an opening angle (out of the page) in a plane substantially perpendicular to that of the page and is restricted to a narrow width within the plane of the page by a collimator as described below. The opening angle of fan beam 20 is a matter of design choice, and fan beam 20 may, indeed, have comparable extent in each dimension within the scope of the invention as described herein and as claimed in any appended claims.

Pencil beam 18 is offset by an angle θ from the plane containing fan beam 20. Angle θ is chosen such that radiation scattered within inspected object 22 (here shown, for example only, as a train car) does not enter any detector 24 of scatter detector array 26 in sufficient intensity to interfere with detection of scatter radiation 28 from pencil beam 18. Additionally, shield 30 may be provided to further shield scatter detector array 26 from radiation scattered from fan beam 20. Collimators (not shown) may be used to further increase the isolation of radiation from pencil beam 18 and fan beam 20.

Angle η between pencil beam 18 and normal 32 to surface 34 of inspected object 22 may advantageously be chosen such that scatter detector array 26 receives scattered radiation 28 which is scattered from pencil beam 18 at an angle Θ with respect to pencil beam 18, where angle Θ is substantially a right angle. The energy of scattered radiation is proportional to the quanitity $[1+\alpha(1-\cos\Theta)]^{-1}$, (where α is proportional to the energy of the beam and equal to unity for an x-ray beam having an energy of 510 keV). Consequently, a photon scattered at an angle Θ of 90° is of higher energy and thus greater penetrating power than a photon scattered directly backward. The energy of the scattered x-ray is generally a substantial fraction of the energy of the incident x-ray and thus the scattered x-ray has considerable penetrating power.

The component of fan beam 20 transmitted through inspected object 22 is detected by transmission detector arrangement 38. In a preferred embodiment of the invention, detector arrangement 38 is an array of x-ray detectors arranged in a row extending out of the page so as to form a slice of an image of attenuation of beam 20 by object 22 at each relative position of the beam and the object.

Inspected object or container 22 may be self-propelled through beams 18 and 20 or may be pulled by a mechanized tractor, or by a conveyor of any sort. Object 22 is depicted in FIG. 1, for example, as a cargo car of a train being pulled along track 36. It is to be recognized that, equivalently, beam 20 may move with respect to object 22 in a direction 40 transverse to the plane of the opening angle of the beam.

Within the scope of the invention, any x-ray detection technology known in the art may be employed for transmission detector arrangement 38 as well as for scatter detection arrangement 26. The detectors may be segmented scintillators or other solid state detectors, for example, or liquid scintillators which may be doped with tin or other metal. Respective output signals from the scatter and transmission detectors 26 and 38 are transmitted to a processor 42, and processed to obtain images of object 22 and its contents, or to obtain other characteristics such, for example, as mass, mass density, mass distribution, mean atomic number, or likelihood of containing targeted threat material, all as known to persons skilled in the art of x-ray inspection.

Additionally shown in FIG. 1 is a second and separate scatter detection arrangement 44 which may be employed in accordance with an alternate embodiment of the invention. A second source 46 emits penetrating radiation which is formed into a scanned pencil beam 48 by rotating chopper wheel 50 so as to scan object 22 from another side from that scanned by scanning pencil beam 18. Penetrating radiation 52 scattered by object 22 is detected by a second scatter detector arrangement 54 which may be shielded by shield 56 from any radiation scattered from fan beam 20.

Figure 2:
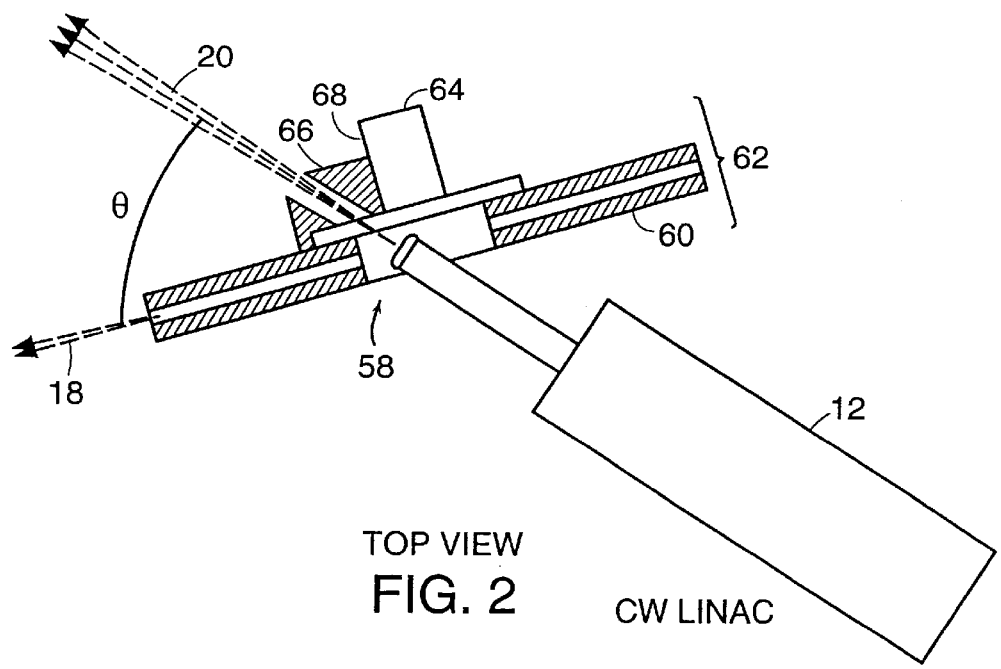
FIG. 2 provides a top view of a chopper wheel embodiment of the present invention for providing both a fan beam and a scanned pencil beam of penetrating radiation.
Figure 3:
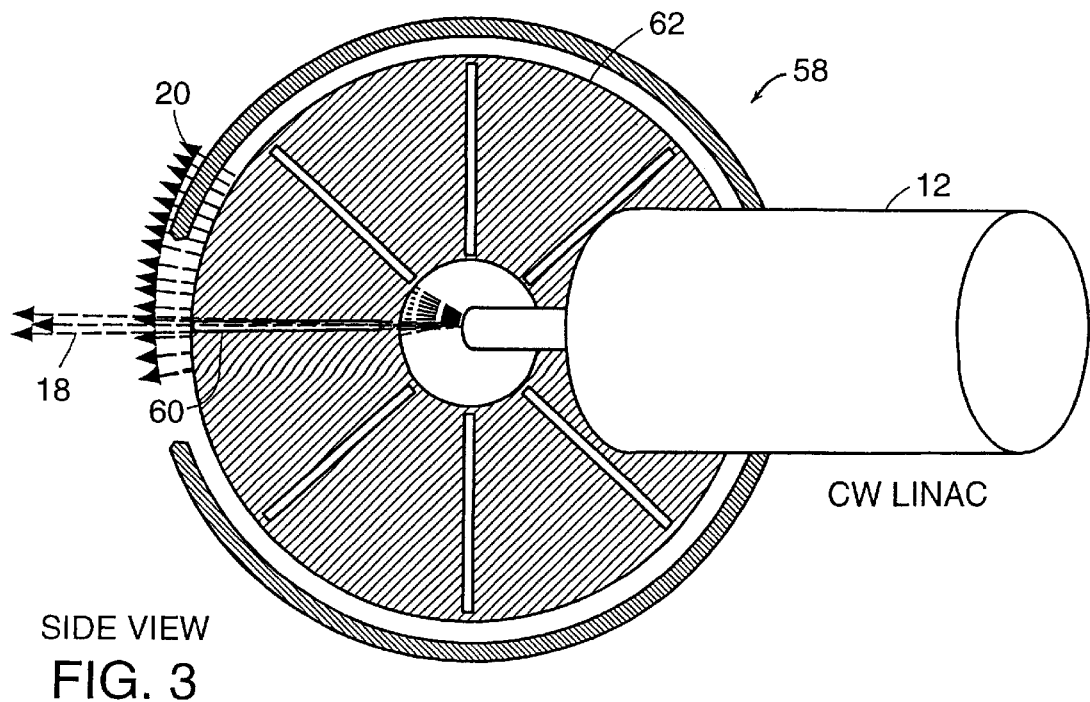
FIG. 3 is a side view of the chopper wheel embodiment of FIG. 2.

Referring now to FIG. 2, a scanning arrangement, designated generally by numeral 58, is shown for forming pencil beam 18 and fan beam 20. Pencil beam 18 is formed by a series of tubular collimators 60 distributed as spokes on rotating wheel 62, shown in this view from the top. Rotating wheel 62 is rotated by means of a rotary actuator such as driving motor 64. Fan beam 20 is formed by slit collimator 66 offset in angle from the plane of rotating wheel 62 by angle θ. In some cases, such as for low energy x-rays, a slot may be advantageously milled in motor housing 68 to reduce attenuation of x-rays from source 12 prior to reaching collimator 66, thereby enhancing the flux of x-rays in fan beam 20. FIG. 3 shows a side view of scanning arrangement 58. Pencil beam 18 is shown emergent from one of eight radial tubular collimators 60 while fan beam 20 emerges to the far side of rotating wheel 62.

Figure 4:
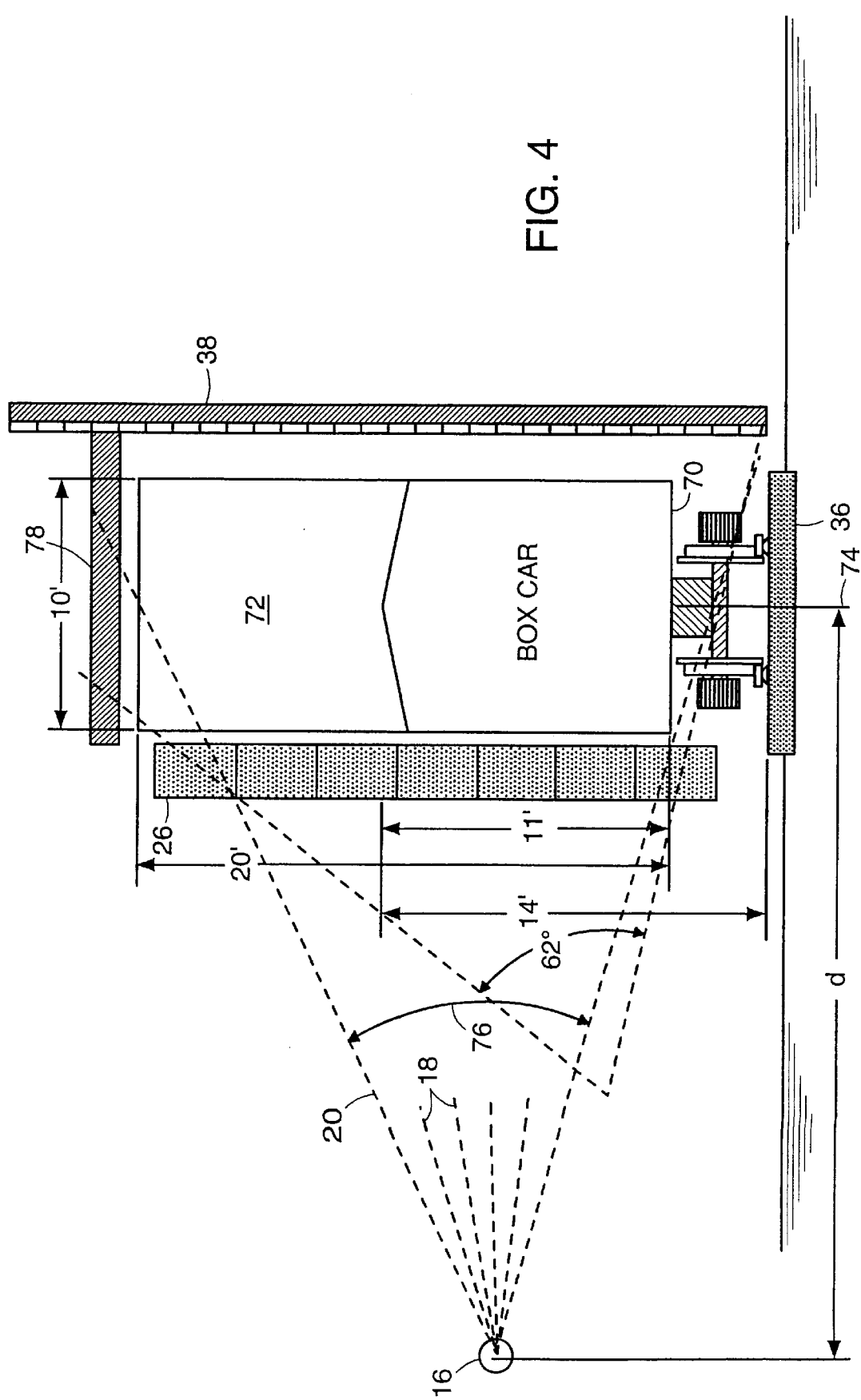
FIG. 4 is a cross-sectional view showing typical dimensions for application of an embodiment of the invention to the inspection of train cars.

Referring now to FIG. 4, a preferred geometry is shown for the inspection of railway cars 70, possibly carrying piggy back sea container 72, in accordance with an embodiment of the invention. Scanning arrangement 16 is displaced a sufficient distance d from center 74 of railway tracks 36 so that opening angle 76 of fan beam 20 covers a substantial portion of car 70. Transmission detector array 38 intercepts all of fan beam 20 that traverses the inspected car 70. Portions of fan beam 20 that do not traverse car 70 may be intercepted, as a matter of safety, by stop 78. Various positions of scanned pencil beam 18 are shown, as is scatter detector array 26. The geometry of FIG. 4 is shown solely by way of example, and indeed the arrangement is quite flexible and in some applications it may be more advantageous to place the x-ray source and the detectors in vertical or slanted arrangements.

The described embodiments of the invention are intended to be merely exemplary and numerous variations and modifications will be apparent to those skilled in the art. All such variations and modifications are intended to be within the scope of the present invention as defined in the appended claims.

We claim:

1. An inspection system for inspecting an object, the system comprising:

(a) a source of penetrating radiation for providing a pencil beam and a fan beam, the pencil beam being noncoplanar with the fan beam;

(b) a first detector arrangement for detecting penetrating radiation from the fan beam transmitted through the object and generating a transmitted radiation signal;

(c) a second detector arrangement for detecting penetrating radiation from the pencil beam scattered by the object and generating a scattered radiation signal; and (d) a controller for determining at least one characteristic of the object based at least on the transmitted and scattered radiation signals.

2. The inspection system as set forth in claim 1, wherein the source of penetrating radiation is an x-ray source.

3. The inspection system as set forth in claim 2, wherein the source of penetrating radiation is a pulsed x-ray source.

4. The inspection system as set forth in claim 2, wherein the source of penetrating radiation is an x-ray tube.

5. The inspection system as set forth in claim 2, wherein the source of penetrating radiation is a linear accelerator.

6. The inspection system as set forth in claim 1, further including a collimator for shaping the fan beam.

7. The inspection system as set forth in claim 1, further including a scanner arrangement for varying the orientation of the pencil beam with respect to the object.

8. The inspection system as set forth in claim 1, wherein the object is in motion with respect to at least one of the pencil and fan beams.

9. A method for characterizing an object, the method comprising:

(a) illuminating the object with penetrating radiation formed into a fan beam defining a plane and simultaneously into a pencil beam noncoplanar with the fan beam;

(b) detecting penetrating radiation from the fan beam transmitted through the object so as to generate a transmitted radiation signal;

(c) detecting penetrating radiation from the pencil beam scattered by the object so as to generate a scattered radiation signal; and (d) determining at least one characteristic of the object based at least on the transmitted and scattered radiation signals.

10. A method according to claim 9, further including:

(e) varying the orientation of the pencil beam with respect to the enclosure.

* * * * *